(12) United States Patent
Vinogradov-Nurenberg

(10) Patent No.: US 9,989,428 B2
(45) Date of Patent: Jun. 5, 2018

(54) BI-DIRECTIONAL FORCE SENSING DEVICE WITH REDUCED CROSS-TALK BETWEEN THE SENSITIVE ELEMENTS

(71) Applicant: Michael Vinogradov-Nurenberg, Sunnyvale, CA (US)

(72) Inventor: Michael Vinogradov-Nurenberg, Sunnyvale, CA (US)

( * ) Notice: Subject to any disclaimer, the term of this patent is extended or adjusted under 35 U.S.C. 154(b) by 64 days.

(21) Appl. No.: 15/257,901

(22) Filed: Sep. 6, 2016

(65) Prior Publication Data

US 2017/0108387 A1    Apr. 20, 2017

Related U.S. Application Data

(60) Provisional application No. 62/243,786, filed on Oct. 20, 2015.

(51) Int. Cl.
*G01L 1/26*    (2006.01)
*G01N 19/02*    (2006.01)

(52) U.S. Cl.
CPC ............... *G01L 1/26* (2013.01); *G01N 19/02* (2013.01)

(58) Field of Classification Search
CPC ................................. G01L 1/26; G01N 19/02
See application file for complete search history.

(56) References Cited

U.S. PATENT DOCUMENTS

| 4,785,673 | A | 11/1988 | Aumard |
| 6,324,918 | B1 | 12/2001 | Gitis et al. |
| 6,363,798 | B1 | 4/2002 | Gitis et al. |
| 2015/0075250 | A1 | 3/2015 | Kosa et al. |

*Primary Examiner* — David M Gray
*Assistant Examiner* — Andrew V Do

(57) ABSTRACT

The invention provides a method and a bi-directional force sensing device with reduced cross-talk between the sensitive elements. The device contains an L-shaped mounting base, which supports force sensitive elements positioned on mutually perpendicular mounting legs of the mounting base. These force sensitive elements are interconnected by a sensor cross-talk reducing member via respective adapters in such a way that one force is translated to the one force sensitive element without affecting or disturbing another force sensitive element, thus reducing the cross-talk between the first and the second force measurements.

12 Claims, 8 Drawing Sheets

US 9,989,428 B2

BI-DIRECTIONAL FORCE SENSING DEVICE WITH REDUCED CROSS-TALK BETWEEN THE SENSITIVE ELEMENTS

FIELD OF THE INVENTION

The present invention relates to the field of tribology and force measurement technique, in particular to a method and apparatus for measuring forces on a friction tester and, more particularly, to bi-directional force sensing device for measuring a normal load and tangential (friction) force in mechanical testers and tribometers. Also, the present invention relates to a sensing circuit for a force sensing device and a method for measuring forces. The invention further relates to a method for reducing cross-talk in a bi-directional force sensing device.

BACKGROUND OF THE INVENTION

Tribology is a science of friction, wear, and lubrication on friction surfaces. Many different types of strain-gauges and other devices for force measuring are known in the art.

U.S. Pat. No. 6,324,918 issued in 2001 to N. Gitis, at all, describes a bidirectional force sensor for measuring two forces applied in two non-parallel directions (FIG. 1). This sensor, which in general is designated by reference numeral 10, is used on a friction tester. The friction tester, which in FIG. 1 is represented by a sensor mounting plate 42, has an upper rod-like test material specimen or probe 44 and a lower disk-like test material specimen 46, which performs rotary motion in the direction indicated by arrow R, while being in contact with a stationary upper specimen 44. This sensor comprises a flexible beam 12 of a rectangular cross section with rigid solid end blocks 14 and 16 at both ends for securing the sensor in a tester. The beam has two symmetrically-shaped through slots cut in mutually perpendicular directions so that they are partially intersected within a body of the beam. Each slot has at its opposite ends notches which are wider than the slots so that the distance from the inner wall of the notch to the outer side surface of the beam is shorter than the distance to this surface from the inner wall of the slot. Strain gauges 38, 40 are attached to mutually perpendicular surfaces at the ends of the beam which are flexible in the direction of the force being measured and are rigid in the perpendicular direction. Under effect of the loading force F1 and of the friction force, the flexible beam acts as a pair of overlapped and mutually perpendicular parallelograms.

A disadvantage of this device is that the upper specimen has a leverage with respect to the point of attachment of the lower specimen, i.e., with respect to its center. As a result, the loading force applied to the lower specimen via the upper probe, as well as the reaction force applied to the probe from the lower specimen create an unbalanced momentum and deformations in the force measurement system.

U.S. Pat. No. 6,363,798 issued in 2002 to N. Gitis, at all, describes another device for measuring a loading force and a friction force in a tribological tester (FIG. 2). This device consists of two deformation-sensitive sensors 51 and 52 for simultaneous equal deformation in two opposite directions for eliminating misbalance created in the measurement system when a single sensor is used. Each sensor comprises a deformable beam 55, 56 having through longitudinal slots 58, 59 extending in different and non-parallel directions and overlapped within the body of the beam. The sensor deforms in one direction under the effect of a loading force 62 measured by two pairs of strain gauges 65, 66 located on opposite sides of the beam near one end of the beam and in another direction under the effect of a friction force 68 measured by another two pairs of strain gauges 70, 71 located on opposite sides of the beam near the other end of the beam. Two sensors are sandwiched between two plates 74, 75 in diagonally symmetrical positions so as to transmit forces between both plates and at the same time to ensure limited freedom of movement between both plates to allow deformations caused by the applied forces. One plate may be attached to the loading unit of the tester (not shown) and another plate may support an upper sample 80 for engagement with the lower sample 90 of the tester.

However, the above sensors have low torsional stability due to the fact that deformable beams in these sensors have elongated shape with reduced cross-sections in the deformable areas. In the tribometers and friction testers the samples for testing are usually mounted to the force sensor not directly but in special holders, which may have significant length (up to several inches) for placing the samples into a testing media (usually fluids or gases) or/and into environmental chambers (heating, cooling, pressure, humidity, etc.).

When a sample mounted in such a holder is brought in contact with moving counter-sample and a normal load is applied to press the samples together a friction force is developed in contact between two samples, which acts in the direction parallel to the direction of motion of a moving sample.

This friction force being applied to a sample mounted in a long holder creates a significant torsional moment in the force sensor directly proportional to the friction force magnitude and to the holder length.

The reduced cross-sections of the flexible beams result in reduction of the torsional stiffness of the force sensor, that causes significant torsional deformation of the force sensor sensitive elements, especially in case when the tangential (friction) force applied to sensor with an offset relative to the longitudinal axis of the sensor, as it usually takes place in friction testers and tribometers (where the force is applied to a specimen attached to the sensor via an elongated holder). This torsional deformation could be a source of additional error of the force measurement. Also, it results in a noticeable tilt of the specimen and specimen holder, increases cross-talk between the normal load and the friction force signals, adding to the measurement error and instability. Besides, under certain conditions, these torsional deformations in combination with moving contacting samples can cause such a parasitic effect as a vibration of the sensor assembly.

SUMMARY OF THE INVENTION

According to one or several aspects of the invention, a bi-directional force sensing device with reduced cross-talk (hereinafter referred to merely as "a sensor device") is provided. The invention also provides a method for reducing cross-talk in a bi-directional force sensing device. The sensor device of the invention also improves mechanical stability, sensitivity, reduces susceptibility to natural frequency resonance, improves accuracy of measurement, increases the dynamic range of forces to be measured and ensures high rigidity in the force transmission directions. The sensor device may find use in tribology and other fields that require measurement of forces with force sensing elements operating in different planes.

According to another aspect of the invention, the proposed sensor device contains a mounting base, preferably of an L-shape configuration, which supports force sensitive elements positioned on mutually perpendicular mounting legs of the mounting base. These force sensitive elements are interconnected by a sensor cross-talk reducing member via respective adapters. The upper part of the probe holder is movably connected with one of the adapters in such a way that the vertical force (e.g., a force transmitted as a reaction from the test specimen to the probe which is pressed to the specimen during the test) is translated to the first force sensitive element without affecting or disturbing the second force sensitive element, thus reducing the cross-talk between the first and the second force measurements.

According to one or several aspects of the invention, the first adapter comprises a roller which is in contact with the upper portion of the probe holder. This allows for an unrestricted motion of the sensor cross-talk reducing member in the direction of the second force, which is translated by the sensor cross-talk reducing member to the second force sensitive element in the direction perpendicular to the direction of the first force, i.e., in the horizontal direction.

The second adapter is made moveable relative to the direction of the first force so as not to interfere with the translation of the vertical force from the probe to the first force sensitive element.

BRIEF DESCRIPTION OF THE DRAWINGS

FIG. 6A is an example of application and electric diagram illustrating connection of bi-directional force sensing device of invention for measuring friction force acting in a direction parallel to the sensor longitudinal axis.

FIG. 6B is an example of application and electric diagram illustrating connection of bi-directional force sensing device of invention for measuring friction force acting in a direction perpendicular to the sensor longitudinal axis.

DESCRIPTION OF THE INVENTION

Figure 1:
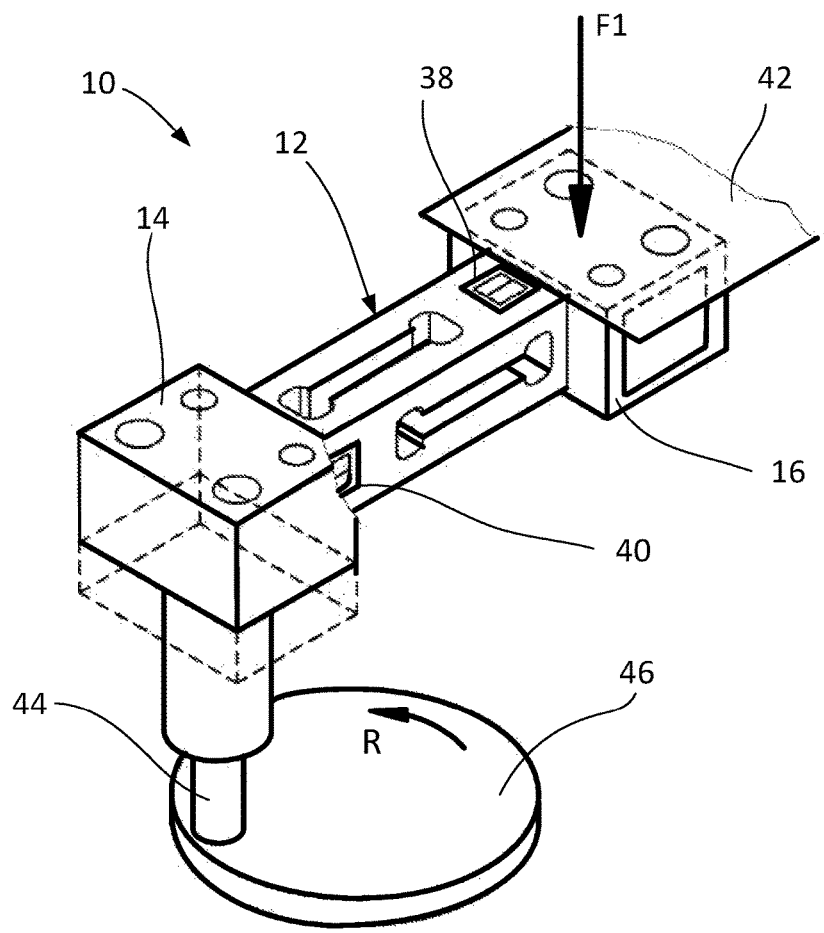
FIG. 1 is a three-dimensional view of a known device for force measurement in a friction tester.
Figure 2:
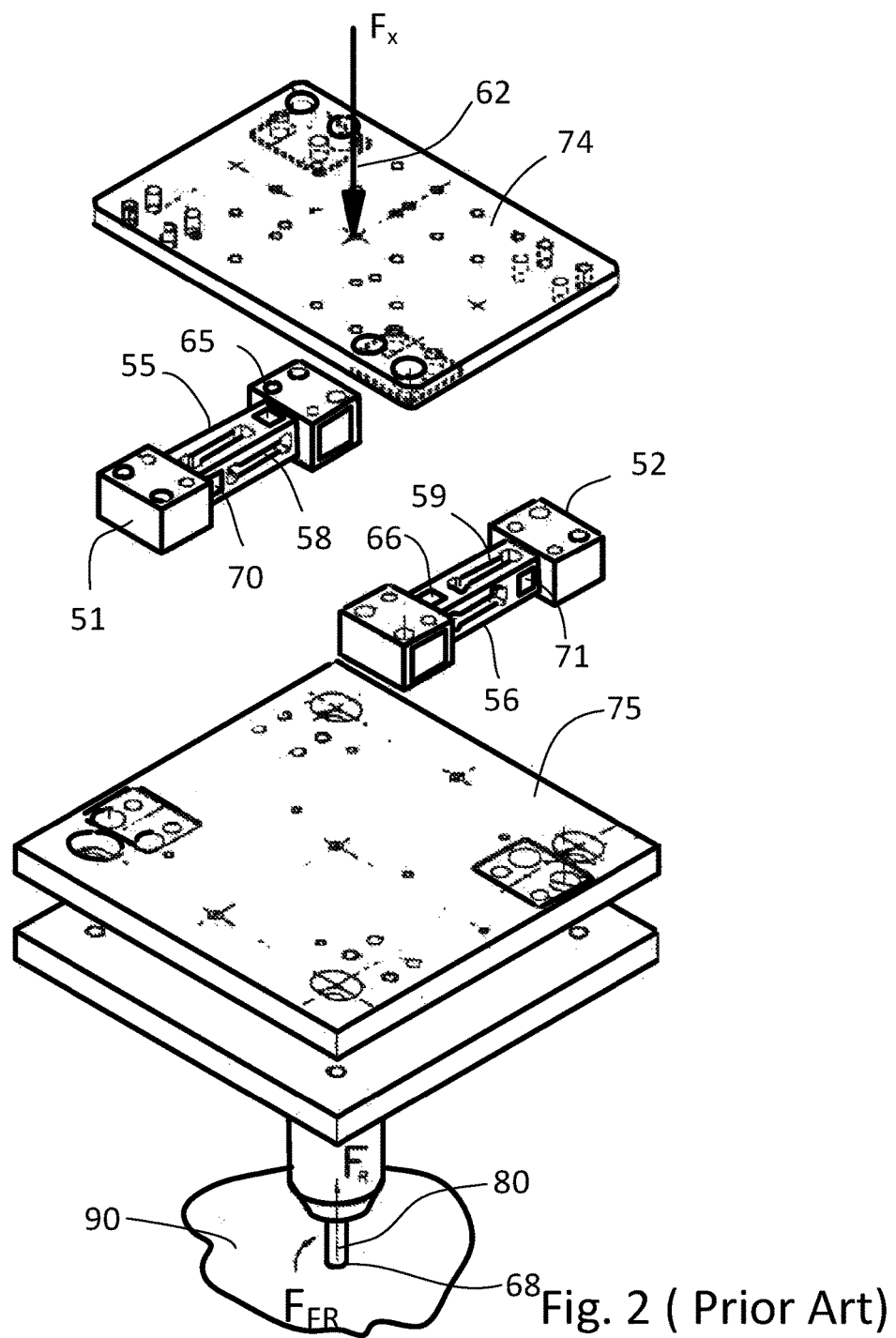
FIG. 2 is a three-dimensional exploded view of another known device for force measurement in a friction tester.
Figure 3:
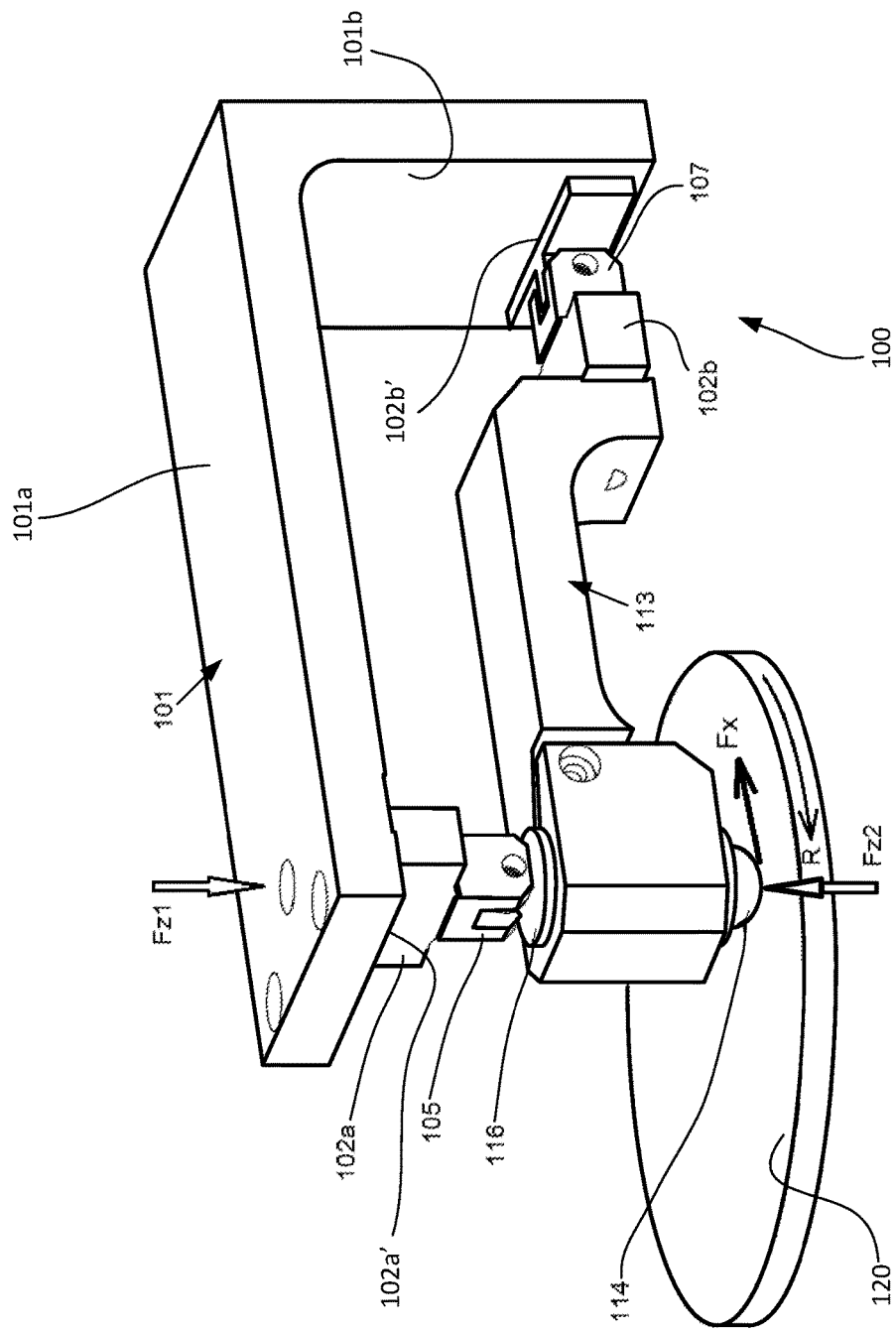
FIG. 3 is a three-dimensional view of a device of the invention for force measurement in a friction tester.

A sensor device of the invention, which in its entity is designated by reference numeral 100, is shown in FIG. 3, which is a three-dimensional view of the sensor device. The sensor device comprises a mounting member or mounting base 101, preferably in the form of an L-shaped body, which supports force sensitive elements 102a and 102b positioned on mutually perpendicular mounting legs 101a and 101b of the mounting base 101, respectively. The first force sensitive element 102a is attached to a first mounting surface 102a' on the leg 101a in such a way that the direction of its maximum force sensitivity is perpendicular to the corresponding mounting leg 101a and coincides with the direction of the first measured force (normal load) Fz1, Fz2 in the tribometer (not shown). A horizontally moveable vertical-force translating adapter 105 attached to the first force sensitive element 102a translates the normal force Fz2 to the first force sensitive element 102a ".

The second force sensitive element 102b is attached to a second mounting surface 102b' on the second mounting leg 101b via a moveable adapter 107 in such a way that the direction of its maximum force sensitivity is perpendicular to the corresponding second mounting leg 101b and coincides with the direction of the second measured force (friction force) Fx in the tribometer (not shown). Reference numeral 113 designates a sensor cross-talk reducing member, one end of which is connected to the horizontally moveable vertical-force translating adapter 105, while the opposite end of which is connected to the second force sensitive element 102b attached to the adapter 107, which in the illustrated case is pivotally moveable. The sensor cross-talk reducing member 113 also supports a test specimen (probe) 114 fixed in a holder 116 so that it is aligned in a vertical direction with the first force sensitive element 102a. The sensor cross-talk reducing member is rigid and translates the lateral friction force Fx from the probe 114 to the second force sensitive element 102b.

The upper part of the probe holder 116 is aligned with the horizontally moveable vertical force translating adapter 105 so that the vertical normal force Fz2 applied to the probe 114 can be translated through the probe holder 116 and the horizontally moveable vertical-force translating adapter 105 to the first force sensitive element 102a.

The second adapter 107, which is movable and in the illustrated case is made as a pivoting joint, allows the second force sensitive element 102b with attached cross-talk reducing member 113 and the probe holder 116 to move (pivot) in the vertical direction, thus not restricting the vertical force Fz2 translation from the probe 114 to the first force sensitive element 102a.

The sensor cross-talk reducing member 113 has high rigidity in the direction parallel to the second (friction) force Fx and allows for translation of the second force Fx to the second force sensitive element 102b while ensuring strictly vertical position of the probe holder 116, thus preventing it from tilting during the test.

The upper part of the probe holder 116 is movably connected with the horizontally moveable vertical-force translating adapter 105 in such a way that the first force Fz2 being translated to the first force sensitive element 102a without affecting or disturbing the second force sensitive element 102b, thus reducing the cross-talk between the first and the second force measurements.

In accordance with another aspect of the invention which is described below with reference to FIG. 3, the horizontally moveable vertical-force translating adapter 105 comprises a roller which is in contact with the upper portion of the probe holder 116, thus allowing for an unrestricted motion of the sensor cross-talk reducing member 113 in the direction of the second force. In other words, the sensor cross-talk reducing member 113 protects the first force sensitive element 102a from the effect of the second (friction) force Fx and protects the second force sensitive element 102b from the effect of the vertical force Fz1, Fz2, thus reducing the cross-talk between the measurement signals of the first and the second force sensitive elements.

In case the sensor device of invention shown in FIG. 3 is used in a tribometer or in a friction tester (not shown), the sensor device is mounted on a vertical loading stage of the tribometer in such a way that the direction of the maximum force sensitivity of the first force sensitive element 102a coincides with the direction of the vertical loading force Fz1. The vertical loading stage of the tribometer moves towards a second movable test specimen 120 (in this example— lower test material disk) to bring the probe 114 in contact with the disk 120 and to apply the normal force Fz1. The reaction force of the same magnitude Fz2 acts in the opposite direction, i.e., from the disk 120 to the probe 114 and through the probe holder 116 and the horizontally moveable vertical-force translating adapter 105 to the first force sensitive element 102a.

In the course of testing, a test material, e.g., a disk-shaped specimen 120 (FIG. 3), is brought into rotation, e.g., in the direction shown by the arrow R, while the loading force Fz1 is applied to the mounting base 101, whereby the probe 114 is kept in contact with the rotating disk 120. The application of force Fz1 causes interaction between the probe 114 and the rotating test material disk 120. The aforementioned interaction generates a friction force Fx shown in FIG. 3 and a reaction force of the same magnitude Fx acting in the opposite direction and translated from the probe 114 through the probe holder 116 and the sensor cross-talk reducing member 113 to the force sensitive element 102b.

It is understood that the force sensitive elements 102a, 102b can be of any type and based on various modes of operation, including strain gauges, capacitive, inductive, piezo-electric, piezo-resonance, optical, and other sensors, used in connection with corresponding signal processing circuitry.

Figure 4:
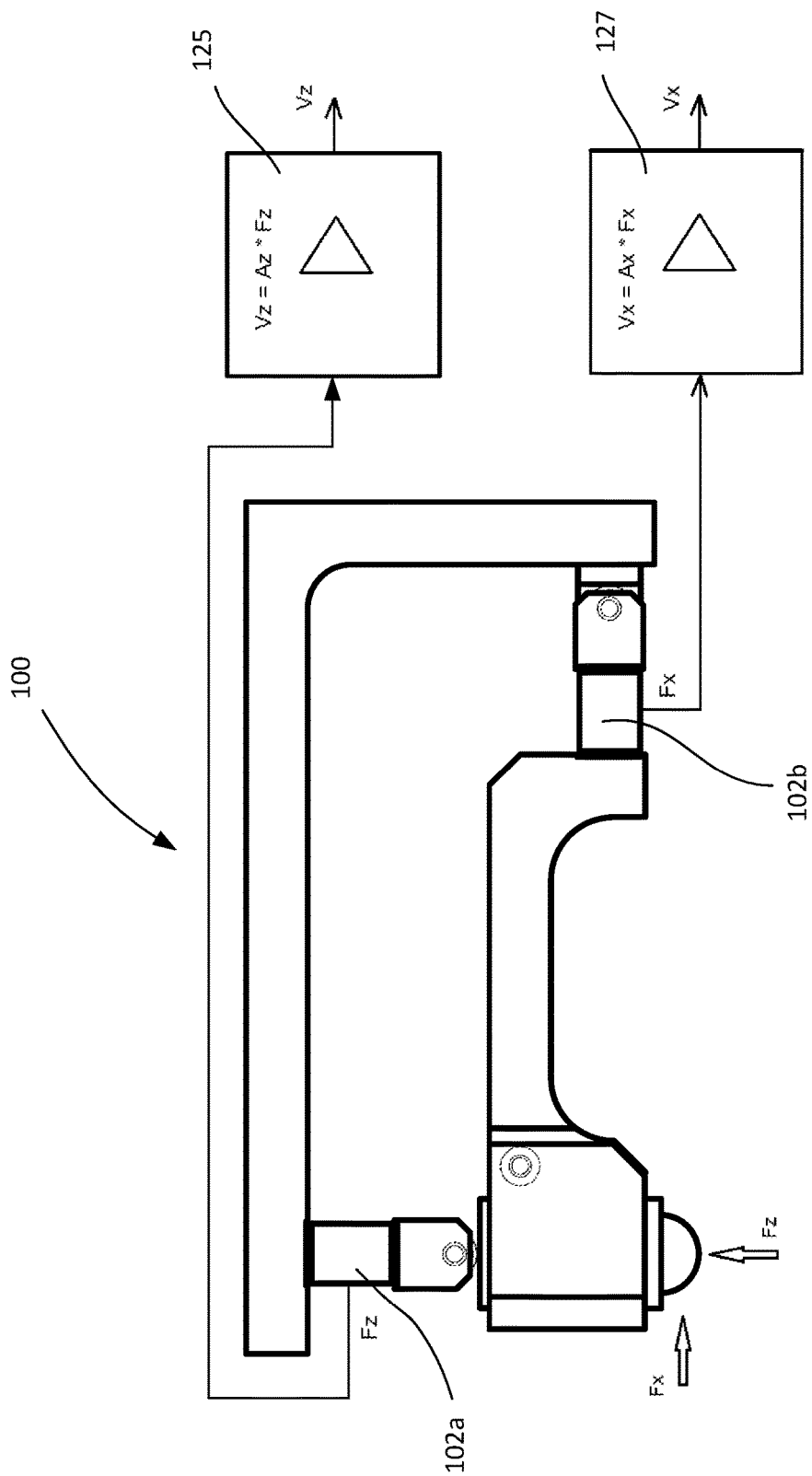
FIG. 4 is an example of an electric circuit of the invention for connection of bi-directional force sensors to the registration and measurement apparatus.

A schematic diagram of a signal processing module for the sensor device of invention is shown in FIG. 4. An output signal from the first force sensitive element 102a is fed to a first signal processor 125 having a signal processing function Az, which generates an output voltage Vz proportional to the magnitude of the normal force Fz2 applied to the probe. The output signal from the second force sensitive element 102b is fed to a second signal processor 127 having a signal processing function Ax, which generates an output voltage Vx proportional to the magnitude of the friction force Fx applied to the probe. The output voltages Vz and Vx can be measured and analyzed by any known voltage measurement or data acquisition apparatus.

The sensor device will be further described and illustrated with reference to other aspects of the invention. In the subsequent descriptions and drawings, the parts and elements of the device similar in their functions with the analogic parts and elements of the device of FIGS. 3 and 4 will be designated by the same reference numerals but with an addition of 100. For example, in the sensor device of FIG. 5, the mounting base is designated by reference numeral 201, the respective force sensitive elements are designated by reference numerals 202a and 202b, etc. Furthermore, since these parts are similar in functions to those of the previously described sensor device, their description will be omitted.

Figure 5:
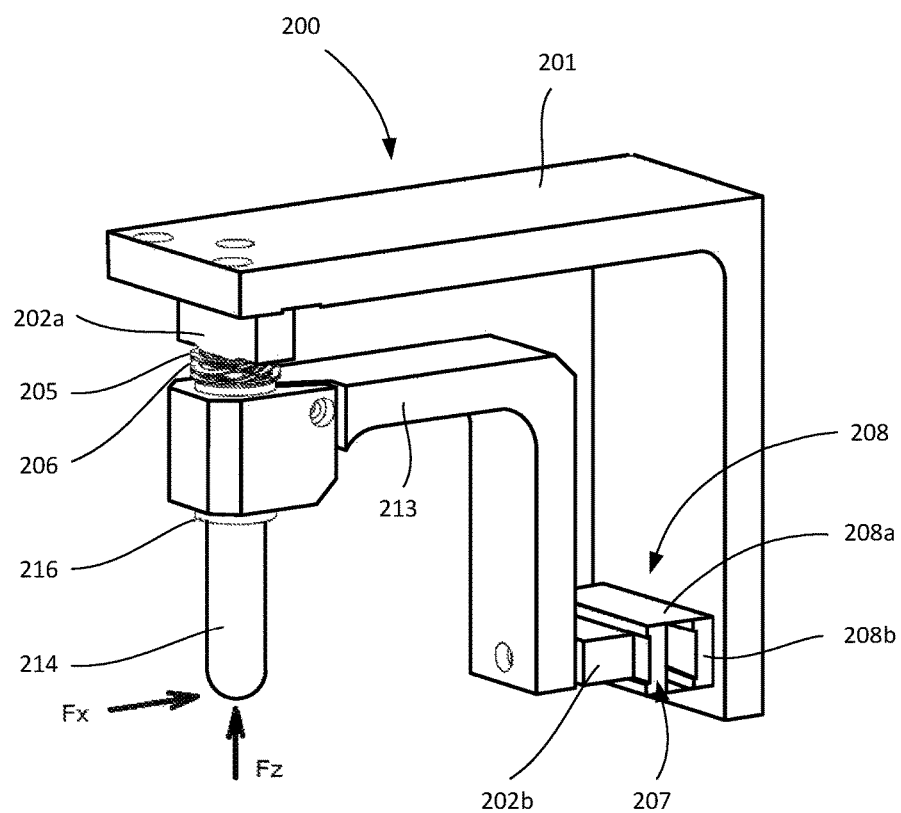
FIG. 5 is a three-dimensional view of another aspect of the device of the invention for force measurement in a friction tester.

According to another aspect of the invention, which is described with reference to FIG. 5, in the sensor device 200 a vertical-force translating adapter 205 comprises a spring 206 positioned between a first force sensitive element 202a and the upper portion of a probe holder 216. It allows for translation of the first (normal) force Fz from a probe 214 through the probe holder 216 and the vertical-force translating adapter 205 with the spring 206 to the first force sensitive element 202a. Also, the spring 206 allows to reduce fluctuations of the normal force Fz which may be caused by non-flatness or runout on the surface of the moving test specimen. The spring 206 has low stiffness in the direction parallel to the second (friction) force Fx and therefore does not restrict motions of a sensor cross-talk reducing member 213 in this direction, thus not restricting translation of the second (friction) force Fx from the probe 214 through the holder 216 and the sensor cross-talk reducing member 213 to a second force sensitive element 202b. As a result, it becomes possible to reduce cross-talk between the force sensitive elements 202a and 202b in measurement of the vertical force (normal load) Fz and the horizontal (friction) force Fx.

In the sensor device 200 a movable adapter 207 comprises a flexible structure made, for example, as a springing device in the form of two parallel sets of flat springs 208a and 208b, which allow the second force sensitive element 202b with the attached sensor cross-talk reducing member 213 to move in the vertical direction parallel to itself.

In accordance with still another aspect of the invention, which is described below with reference to FIGS. 6A and 6B, a second force sensitive element 302b comprises at least two components 302b-1 and 302b-2 positioned at a distance from each other in such a way that the directions of their maximum force sensitivity are parallel to each other, perpendicular to a corresponding leg 301b of an L-shaped mounting base 301, and coincide with the direction of the second measured force (friction) Fx in the tribometer. A sensor cross-talk reducing member 313 is attached to the components 302b-1 and 302b-2 of the force sensitive element 302b preferably at the median position between these components. Such an arrangement makes it possible to support the sensor cross-talk reducing member 313 both in the direction parallel to the second (friction) force Fx and in the third direction Y perpendicular to the first (normal) force Fz and to the second (friction) force Fx.

Figure 6A:
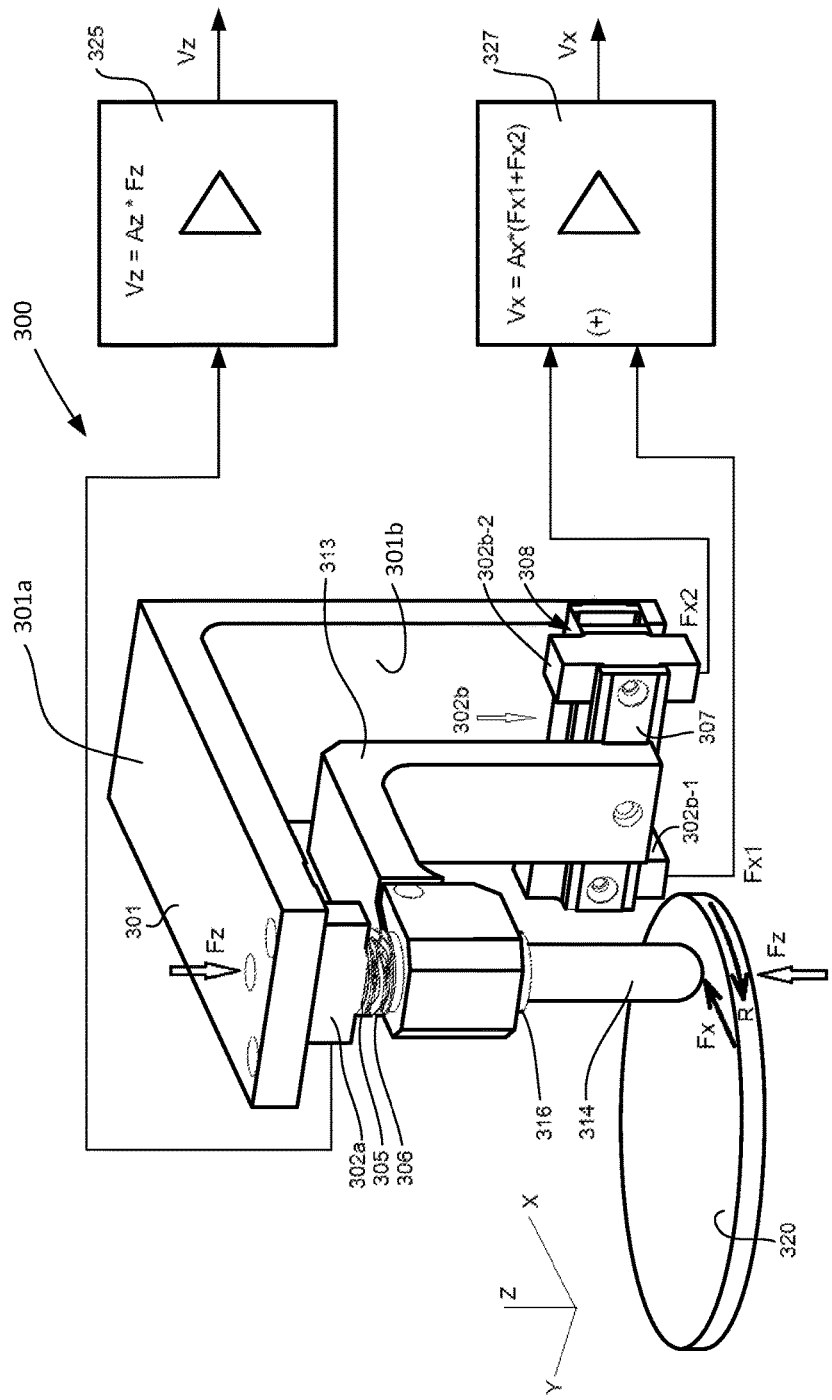
FIGS. 6A and 6B are three-dimensional views of the sensor devices according to other aspects of the invention with electric diagrams illustrating connection of bi-directional force sensing device of invention for measuring friction force acting in different directions in horizontal plane.

FIG. 6A represents an example application of a sensor device in accordance with another aspect of the invention, wherein the sensor device is used in a tribometer or in a friction tester. FIG. 6A also shows a schematic diagram of a signal processing module. In this case, the sensor device 300 with a probe 314 is positioned relative to a rotating test specimen 320 in such a way that the friction force Fx developed in the contact between the probe 314 and the specimen 320 is acting parallel to the sensor cross-talk reducing member 313. In this case, the components 302b-1 and 302b-2 of the sensitive element 302b that support the sensor cross-talk reducing member 313 may be deformed in the same directions: both of them are either compressed or extended (depending on the direction of the test specimen rotation). Output signals from the components 302b-1 and 302b-2 are fed to a second signal processor 327 having a signal processing function Ax, which generates the output voltage Vx proportional to the sum of the signals Fx1 and Fx2 from the components 302b-1 and 302b-2, respectively. The resulting signal is proportional to the total magnitude of the friction force Fx applied to the probe 314 in the direction of axis X. On the other hand, an output signal from a first force sensitive element 302a is fed to a first signal processor 325 having a signal processing function Az, which generates an output voltage Vz proportional to the magnitude of the normal force Fz applied to the probe 314. The output voltages Vz and Vx can be measured and analyzed by any known voltage measurement or data acquisition apparatus.

Figure 6B:
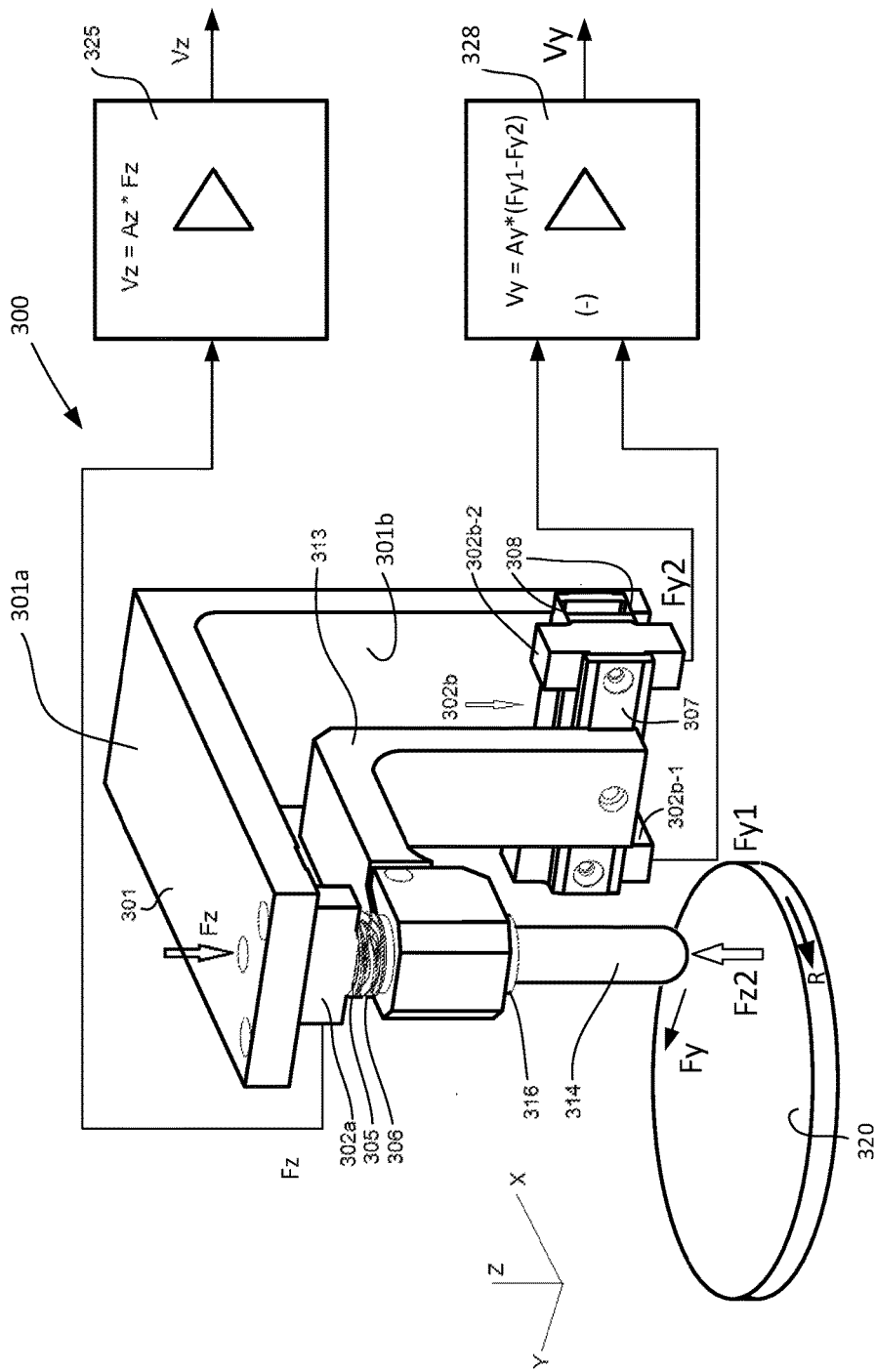

FIG. 6B illustrates implementation of the sensor device 300 of FIG. 6A along with the measurement circuit of the latter for measuring the normal force Fz in combination with a friction force Fy acting in the direction of axis Y.

In this case the sensor device with the probe 314 is positioned relative to the rotating test specimen 320 in such a way that the friction force Fy developed in contact between the probe 314 and the test specimen 320 is acting perpendicular to the sensor cross-talk reducing member 313. During the test, the components 302b-1 and 302b-2 of the sensitive element 302b that support the sensor cross-talk reducing member 313 are deformed in the opposite directions: one of them is compressed while another one is extended. In this case the measured value of the friction force Fy is the total deviation of the output signals of both components of the force sensitive element 302b from their corresponding unloaded states. The output signals Fy1 and Fy2 from the force sensitive element components 302b-1 and 302b-2, respectively, are fed to a second signal processor 328 having a signal processing function Ay, which generates an output voltage Vy proportional to the difference between the signals Fy1 and Fy2 from the sensitive element components 302b-1 and 302b-2. The resulting voltage is proportional to the magnitude of the friction force Fy applied to the probe 314.

An output signal Fz from the first force sensitive element 302a is fed to the first signal processor 325 having a signal processing function Az, which generates an output voltage Vz proportional to the magnitude of the normal force Fz applied to the probe 314. The output voltages Vz and Vy can be measured and analyzed by any known voltage measurement or data acquisition apparatus.

Figure 7:
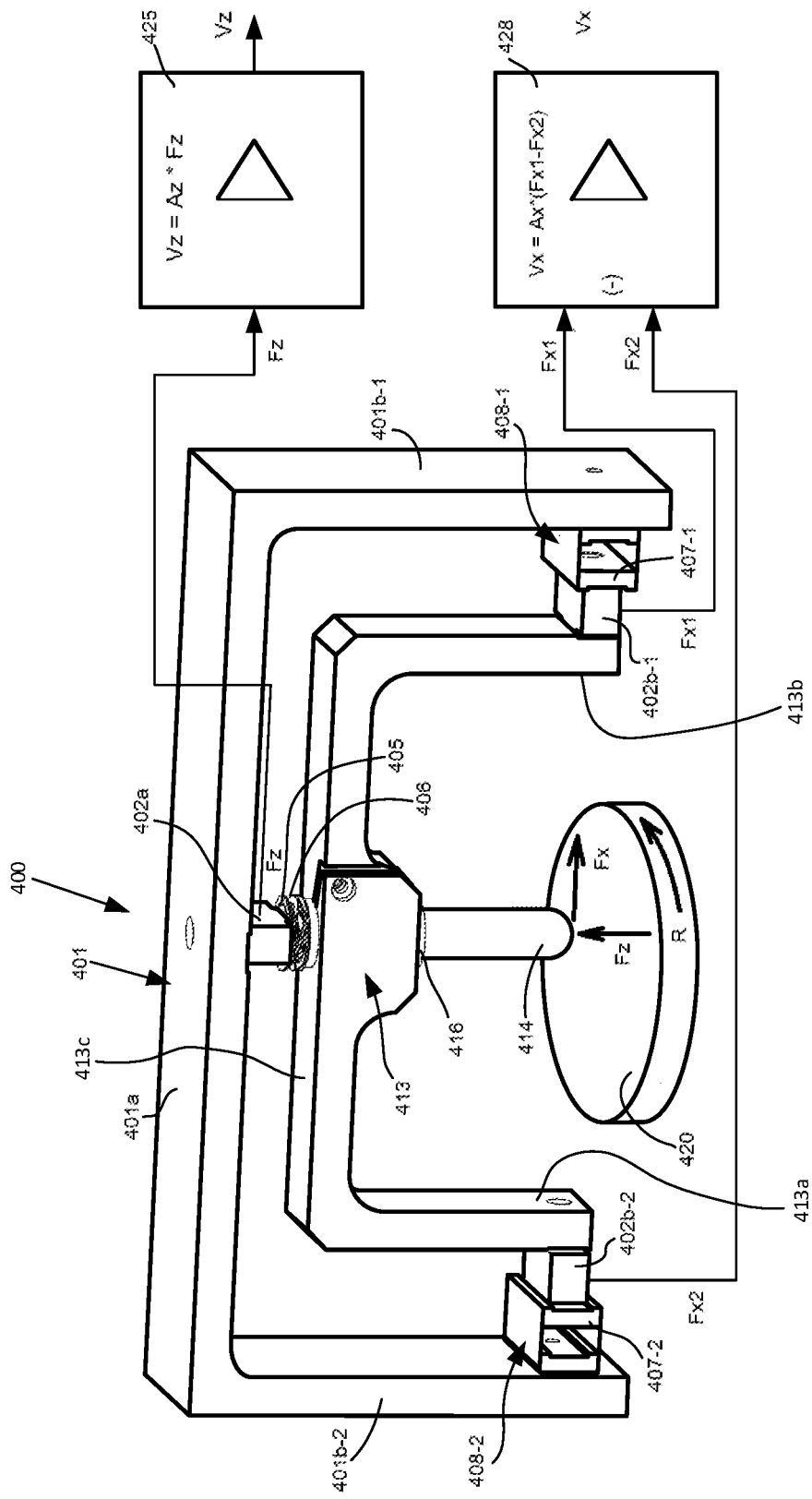
FIG. 7 is a three-dimensional view of a sensor device according to yet another aspect of the invention, with an example of application and electric diagram for force measurement in a friction tester.

In accordance with still another aspect of the invention, a sensor device 400 shown in FIG. 7 has a mounting base 401, which is made as a U-shaped body having an intermediate portion 401a arranged horizontally and two vertical legs 401b-1 and 401b-2 that extend vertically downward and parallel to each other from the ends of the horizontal intermediate portion 401a.

A first force sensitive element 402a is attached to the mounting base at a first mounting surface at the center of the intermediate portion 401a. In this case, the sensor device 400 of invention is provided with at least two movable adapters 407-1 and 407-2 attached to the opposite vertical legs 401b-1 and 401b-2 on first and second mounting areas, respectively. The aforementioned first and second mounting areas constitute a second mounting surface.

A second force sensitive element consists of at least two force sensitive components 402b-1 and 402b-2 attached to two movable adapters 407-1 and 407-2, correspondingly, in such a way that the directions of their maximum sensitivity to the measured forces are parallel and in line with each other and coincide with the direction of the second measured force (friction) Fx in the tribometer. At the same time, these directions are perpendicular to the direction of maximum force sensitivity inherent in the first force sensitive element 402a that senses the vertical force Fz.

A sensor cross-talk reducing member 413, which in this case has a U-shaped configuration, is positioned between two force sensitive components 402b-1 and 402b-2 of the second force sensitive element. The ends of vertical legs 413a and 413b that extend downward from a central section 413c of the sensor cross-talk reducing member 413 are attached to the force sensitive components 402b-1 and 402b-2, respectively.

A test probe 414 is fixed in a holder 416 positioned at the center of the sensor cross-talk reducing member 413 and is aligned with the first force sensitive element 402a. A vertical force translating adapter 405 is attached to the first force sensitive element 402a and is intended for translating the vertical force Fz applied to the probe 414 to the first force sensitive element 402a.

Friction force Fx developed in the interface between the probe 414 and a rotating test specimen 420 is translated through the probe holder 416 and the sensor cross-talk reducing member 413 to the force sensitive components 402b-1 and 402b-2 of the second force sensitive element and causes the force sensitive components 402b-1 and 402b-2 to deform in the opposite ways, e.g., the force sensitive component 402b-1 is compressed while the force sensitive component 402b-2 is extended (see FIG. 7), or vice versa. In this case, the output signals from the force sensitive components 402b-1 and 402b-2 are changed in the opposite directions (e.g., the signal from the force sensitive component 402b-1 increases, while the signal from the force sensitive component 402b-2 decreases). A differential signal processing module 428 with the schematic diagram similar to the one shown in FIG. 6B generates an output voltage Vx proportional to the difference between the signals Fx1 and Fx2 from the force sensitive components 402b-1 and 402b-2, which in turn is proportional to the magnitude of the friction force Fx applied to the probe 414. The output signal Fz from the first force sensitive element 402a is fed to a first signal processor 425 having a signal processing function Az, which generates the output voltage Vz proportional to the magnitude of the vertical force Fz applied to the probe 414. The output voltages Vz and Vx can be measured and analyzed by any known voltage measurement or data acquisition apparatus.

In the sensor device 400 shown in FIG. 7 the vertical force translating adapter 405 comprises a spring 406 positioned between the first force sensitive element 402a and the upper portion of the probe holder 416. The movable adapters 407-1 and 407-2 comprise springing devices, e.g., as sets of flat springs 408-1 and 408-2, respectively. It is understood that the movable adapters 407-1 and 407-2 are not limited by the devices shown in the drawing and may comprise moving elements of a different types, including linear, rolling, pivoting, etc., having high stiffness in the direction parallel to the direction of the friction force Fx and low stiffness in the direction parallel to the direction of the vertical force (normal load) Fz, thus presenting no restriction for translating the vertical force Fz from the probe 414 to the first force sensitive element 402a. It is further understood that the vertical force translating adapter 405 may be embodied in a manner different from one shown in the drawing and may comprise a flexible unit, rollers, springs, etc., having high stiffness in the direction parallel to the direction of the vertical force (normal load) Fz and low stiffness in the direction parallel to the direction of the horizontal force (friction) Fx. In other words, the translation of the second measured force Fx from the probe 414 to the second force sensitive components 402b-1 and 402b-2 is carried out without interference with the translation of the vertical force Fz to the first force sensitive element 402a, thus reducing a cross-talk between the measured forces.

It is also understood that the force sensitive element 402a and force sensitive components 402b-1, 402b-2 may be of any type and based on various modes of operation, including strain gauges, capacitive, inductive, piezo-electric, piezo-resonance, optical, and other sensors, used in connection with corresponding signal processing circuitry.

The invention has been described and illustrated in various aspects with reference to specific structures and drawings. It is understood, however, that these structures and drawings are given only as examples and should not be construed as limiting the area of application of the invention. Therefore, any changes and modifications are allowed provided that they do not depart from the scope of the attached claims. For examples, more than two force sensitive elements, i.e., sensors, can be used. The mounting base may have a shape different from the L-like shape. The second force sensitive element may be directly attached to the vertical leg of the mounting base and attached to the sensor cross-talk reducing member via a movable adapter. The adapters may have different shapes and designs, and the sensor device of the invention may be used not necessarily on a tribometer but on any other tester where force measurement is needed. It is understood that features in accordance with various aspects can be used in various combinations. For examples, the vertical force translating adapters as rollers or springs can be combined with second adapters as springs, pivotal devices, linearly moveable devices, or as other devices suitable for accomplishing the objects of the invention within the scope of the claims.

The invention claimed is:

1. A bi-directional force sensing device for measuring a first force acting in a first direction and a second force acting in a second direction which is different from the first direction and is not parallel thereto, with reduced cross-talk between the measured forces, the force sensing device comprising:
   a mounting base having a first mounting surface and a second mounting surface, the second mounting surface being not parallel to said first mounting surface;
   at least two force sensitive elements comprising a first force sensitive element for sensing the first force and a second force sensitive element for sensing the second force, wherein the first force sensitive element is connected to the mounting base at the first mounting surface and the second force sensitive element is connected to the mounting base at the second mounting surface;
   a test specimen/probe holder for supporting a test specimen or a test probe, said test specimen/probe holder having an axis that coincides with the first direction;
   a first force translating adapter that is moveable in the second direction and that connects the test specimen/probe holder with the first force sensitive element;
   a second adapter that is moveable relative to the first direction and that is connected to the second force sensitive element; and
   a sensor cross-talk reducing member one end of which is connected to the test specimen/probe holder and another end of which is connected to the second mounting surface via the second force sensitive element and the second adapter.

2. The bi-directional force sensing device according to claim 1, wherein the first force and the second force are acting in mutually perpendicular directions.

3. The bi-directional force sensing device according to claim 2, wherein the mounting base comprises an L-shaped body having a first leg and a second leg and wherein the first mounting surface is located on the first leg and the second mounting surface is located on the second leg, the first leg and the second leg being perpendicular to each other.

4. The bi-directional force sensing device according to claim 3, wherein the first force translating adapter comprises a roller.

5. The bi-directional force sensing device according to claim 4, wherein the second adapter comprises a pivoting member.

6. The bi-directional force sensing device according to claim 2, wherein the first force translating adapter comprises a roller.

7. The bi-directional force sensing device according to claim 6, wherein the second adapter comprises a pivoting member.

8. The bi-directional force sensing device according to claim 2, wherein the first force translating adapter comprises a springing device and the second adapter comprises a springing device.

9. The bi-directional force sensing device according to claim 2, wherein the mounting base comprises a U-shaped body having an intermediate portion with two ends, and two legs extending downward from the two ends; the first mounting surface being on the intermediate portion, the second mounting surface comprising two mounting areas, wherein one mounting area is located on one leg, another mounting area is located on another leg; and the sensor cross-talk reducing member is located between the two legs and supports the probe/specimen holder with the test specimen/probe.

10. The bi-directional force sensing device according to claim 9, wherein the second force sensitive element comprises two force sensitive components, the second adapter comprises two movable members, the sensor cross-talk reducing member being connected to said one mounting area via one force sensitive component and one movable member and being connected to said another mounting area via another force sensitive component and another movable member.

11. The bi-directional force sensing device according to claim 10, wherein the first force translating adapter is a spring.

12. The bi-directional force sensing device according to claim 11, wherein the second adapter comprises two springing devices.

* * * * *